(12) United States Patent
Truckai

(10) Patent No.: US 11,871,984 B2
(45) Date of Patent: Jan. 16, 2024

(54) SYSTEMS AND METHODS FOR FEMALE CONTRACEPTION

(71) Applicant: Cirrus Technologies KFT, Budapest (HU)

(72) Inventor: Csaba Truckai, Saratoga, CA (US)

(73) Assignee: Meditrina, Inc., San Jose, CA (US)

( * ) Notice: Subject to any disclaimer, the term of this patent is extended or adjusted under 35 U.S.C. 154(b) by 0 days.

(21) Appl. No.: 14/793,591

(22) Filed: Jul. 7, 2015

(65) Prior Publication Data

US 2016/0030109 A1 Feb. 4, 2016

Related U.S. Application Data

(60) Provisional application No. 62/021,334, filed on Jul. 7, 2014, provisional application No. 62/053,676, filed on Sep. 22, 2014.

(51) Int. Cl.
| | |
|---|---|
| *A61F 6/20* | (2006.01) |
| *A61B 18/14* | (2006.01) |
| *A61F 6/22* | (2006.01) |
| *A61B 17/42* | (2006.01) |
| *A61B 17/12* | (2006.01) |

(Continued)

(52) U.S. Cl.
CPC .... *A61B 18/1492* (2013.01); *A61B 17/12031* (2013.01); *A61B 17/12159* (2013.01); *A61B 17/42* (2013.01); *A61F 6/22* (2013.01); *A61B 17/320016* (2013.01); *A61B 18/02* (2013.01); *A61B 2017/320791* (2013.01); *A61B 2017/4233* (2013.01); *A61B 2018/0022* (2013.01); *A61B 2018/00291* (2013.01); *A61B 2018/00559* (2013.01); *A61B 2018/00577* (2013.01); *A61B 2018/00607* (2013.01); *A61B 2018/00702* (2013.01); *A61B 2018/00791* (2013.01); *A61B 2018/00875* (2013.01); *A61B 2018/00886* (2013.01); *A61B 2218/007* (2013.01)

(58) Field of Classification Search
CPC ... A61F 6/20; A61F 6/22; A61F 6/225; A61B 17/12031; A61B 17/12159; A61B 17/42; A61B 17/320016; A61B 17/1204; A61B 17/12022; A61B 2017/1125; A61B 2017/4233; A61B 2017/320791; A61B 2018/00559; A61B 2018/1492; A61B 2018/0022; A61B 2018/00291; A61B 2018/00577; A61B 2018/00607; A61B 18/02; A61B 2017/12059; A61B 2017/320016; A61B 17/4233; A61B 18/1492
See application file for complete search history.

(56) References Cited

U.S. PATENT DOCUMENTS

| | | | |
|---|---|---|---|
| 4,016,881 A | 4/1977 | Rioux et al. | |
| 5,122,137 A * | 6/1992 | Lennox | A61B 18/1206 606/40 |

(Continued)

FOREIGN PATENT DOCUMENTS

WO WO 2016/007545 1/2016

*Primary Examiner* — Camtu T Nguyen
(74) *Attorney, Agent, or Firm* — Levine Bagade Han LLP

(57) ABSTRACT

The present invention relates to medical devices and methods for treating and occluding a female patient's fallopian tubes to provide birth control or sterilization, where such birth control/sterilization can be short term, long term, or permanent.

19 Claims, 14 Drawing Sheets

(51) Int. Cl.
   *A61B 18/02*      (2006.01)
   *A61B 18/00*      (2006.01)
   *A61B 17/32*      (2006.01)
   *A61B 17/3207*    (2006.01)

(56) References Cited

U.S. PATENT DOCUMENTS

| | | | | |
|---|---|---|---|---|
| 5,303,719 | A * | 4/1994 | Wilk | A61B 18/24 |
| | | | | 128/831 |
| 5,891,141 | A * | 4/1999 | Rydell | A61B 18/1485 |
| | | | | 606/167 |
| 6,042,590 | A * | 3/2000 | Sporri | A61B 17/12022 |
| | | | | 606/135 |
| 6,066,139 | A * | 5/2000 | Ryan | A61B 18/1206 |
| | | | | 606/135 |
| 7,905,880 | B2 * | 3/2011 | Harrington | A61B 17/12159 |
| | | | | 606/28 |
| 8,528,563 | B2 | 9/2013 | Gruber | |
| 2007/0265613 | A1 * | 11/2007 | Edelstein | A61B 18/1442 |
| | | | | 606/37 |
| 2008/0071269 | A1 | 3/2008 | Hilario et al. | |
| 2008/0154256 | A1 * | 6/2008 | Payne | A61F 6/225 |
| | | | | 128/831 |
| 2010/0262177 | A1 * | 10/2010 | Frigstad | A61B 17/12022 |
| | | | | 606/191 |
| 2013/0211321 | A1 | 8/2013 | DuBois et al. | |
| 2016/0270846 | A1 * | 9/2016 | Truckai | A61F 6/22 |

* cited by examiner

SYSTEMS AND METHODS FOR FEMALE CONTRACEPTION

RELATED APPLICATIONS

The present disclosure is a non-provisional application of U.S. provisional application Ser. No. 62/021,334 filed Jul. 7, 2014 and U.S. provisional application 62/053,676 filed Sep. 22, 2014. Each of which is incorporated by reference herein.

FIELD OF THE INVENTION

The present invention relates to medical devices and methods for treating and occluding a female patient's fallopian tubes to provide birth control or sterilization, where such birth control/sterilization can be short term, long term, or permanent.

BACKGROUND

Female sterilization typically involves occluding a patient's fallopian tubes, with various procedures using laparoscopic or minimally invasive trans-cervical approaches. One procedure involves placing flexible coil-like devices into the fallopian tubes which are made of polyester fibers and metal wires. Tissue in-growth into the implanted devices can block the fallopian tubes. However, such implants are worrisome due to potential unknown long term effects. Further, the metallic implanted devices may raise concerns about other future medical procedures, such as use of MRI.

SUMMARY OF THE INVENTION

The tubal occlusion procedure described herein is a minimally invasive procedure in which a device can be introduced into the patient's uterine cavity trans-cervically. Variations of the procedure do not leave an implant in the patient's body to minimize the risk of infection and other potential complications.

The present disclosure includes systems, devices, and methods for preforming a desired treatment in a tube, lumen, or body passageway, such as a fallopian tube. The features and aspects of the various illustrated devices and methods can be combined as needed.

In one example, a device or system according to the present disclosure includes an elongated flexible catheter configured for trans-cervical access to a site in the fallopian tube; a first electrode and a second electrode spaced apart at a working end of the flexible catheter; and a tissue cutting mechanism carried by the working end and located between the first electrode and second electrode.

In one variation, the system includes first and second electrodes that extend axially over at least 1 cm of the working end.

In an additional variation, the system can include a cutting mechanism having at least a first sharp cutting edge carried by a moveable outer sleeve, where the first electrode is positioned on the moveable outer sleeve.

In another variation, the cutting mechanism is intermediate the proximal and distal regions of the electrodes. Variations of the cutting mechanism can include cutting mechanisms having an inner member disposed in a passageway of the moveable outer sleeve.

The devices and systems can further include a negative pressure source communicating with a flow pathway in the catheter with an open termination in the working end. In additional variations, the system can further comprise an RF source and a controller operatively coupled to the first and second electrode.

In certain variations, the first and second electrodes comprise opposite polarity electrodes when transmitting energy from the RF source.

The system can include any additional safeguard measures, including a controller that terminates energy delivery to the electrodes in response to at least one of time, impedance, capacitance, and temperature.

In another variation, the disclosure includes a catheter system for occluding a fallopian tube. In one such example the catheter includes an elongated catheter having a working end carrying a thermal ablation portion configured to ablate tissue in a fallopian tube lumen; and a tissue cutting mechanism carried by the working end configured to cut tissue in the fallopian tube lumen.

The catheter system can further include a negative pressure source communicating with a flow pathway in the catheter having an open termination in the working end.

The devices described herein can include thermal ablation structures that provides at least one of a heating treatment or a cryogenic treatment. Alternatively, or in addition, the thermal ablation mechanisms can perform thermal ablation using at least one of RF energy, light energy, microwave energy, resistive heating, inductive heating or ultrasound.

In an additional variation, the thermal ablation portion comprises a first portion and a second portion spaced apart on either side of the tissue cutting mechanism, where the first portion is moveable relative to the second portion.

The catheter system can also include a tissue cutting mechanism that includes at least one of a sharp blade edge, an abrasive element and a sharp puncturing element.

Variations of the systems and devices can include one or more expandable balloons.

Additionally, the systems can include a biodegradable implant configured for deployment in the fallopian tube lumen. Such an implant can be barbed, porous, and/or include one or more bioactive substances.

In an additional variation, the present disclosure includes one or more methods for occluding a fallopian tube or any other tubular structure in the body. For example, such a method can include advancing a probe trans-cervically to a site in the fallopian tube; applying energy from the probe to ablate fallopian tube tissue at the site; actuating a cutting mechanism of the probe to cause bleeding within the site wherein the bleeding facilitates adhesion of walls of the fallopian tube to provide permanent occlusion. In one variation, the method can include advancing the probe over a guidewire.

The method can include energy applications such as RF energy, light energy, microwave energy, resistive heating, inductive heating or ultrasound. The actuating step can include actuating at least one of a sharp blade edge, an abrasive element and a sharp puncturing element.

In another variation, the method can include a method for female sterilization comprising: ablating the endothelial and/or endometrial cells in an elongated segment of the lumen of a fallopian tube; and treating an intermediate portion of said lumen segment to cause Asherman's syndrome in said intermediate portion to thereby occlude the lumen.

In one aspect of the method of the invention, a physician uses RF energy to ablate a thin layer of tissue in a segment of a fallopian tube which can be performed very rapidly, for example in 10 to 60 seconds. A second step involves inducing a wound healing response (for example by cutting or otherwise damaging the tissue within the segment). These acts can be accomplished very quickly. The wound healing response causes an adhesion of the walls in the segment allowing for closure of the fallopian tube. In certain cases, the closure can be permanent.

In another method under the present disclosure, an elongated segment of a fallopian tube is damaged by cutting, abrading, puncturing or the like to cause a wound healing response which again can cause an adhesion of the fallopian tube walls. In this method, the damage at least partially de-nudes the tube walls of endothelial cells, and the length of the damaged segment is sufficient such that an adhesion occludes the segment before new endothelial cells migrate inwardly from the ends of the damaged segment.

The details of one or more embodiments of the invention are set forth in the accompanying drawings and the description below. Other features, objects, and advantages of the invention will be apparent from the description and drawings, and from the claims.

BRIEF DESCRIPTION OF THE DRAWINGS

FIG. 4A shows use of abrasive wires to damage and abrade the surface layers of an elongate segment of a fallopian tube lumen.

DETAILED DESCRIPTION OF THE INVENTION

Figure 1:
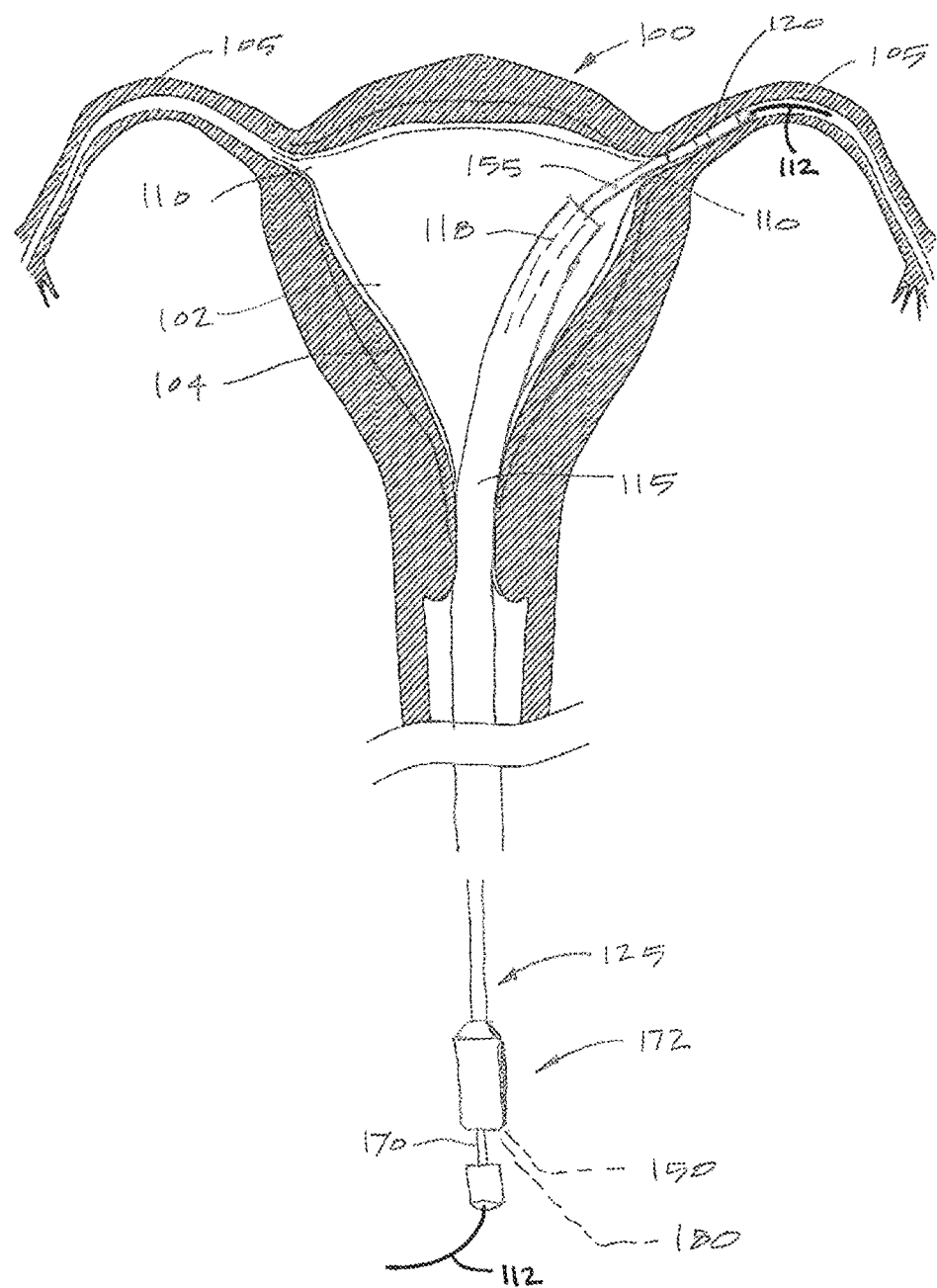
FIG. 1 is a representation of a uterus and the use of an endoscope to introduce a working end of a treatment probe into a fallopian tube.

A method for female sterilization is described below wherein a female's fallopian tubes are occluded in a minimally invasive procedure. Referring to FIG. 1, a schematic representation of a uterus 100 is shown, including a uterine cavity 102 lined with endometrial tissue 104. The fallopian tubes 105 extend from the uterine cavity 102 at the tubal ostia 110. In FIG. 1, it can be seen that an endoscope 115 with a working channel 118 is introduced trans-cervically into the uterine cavity 102. The distal end of the endoscope can be positioned near the tubal ostium 110. The working end 120 of treatment probe 125 is introduced through the working channel 118 and into a fallopian tube 105.

Figure 2A:
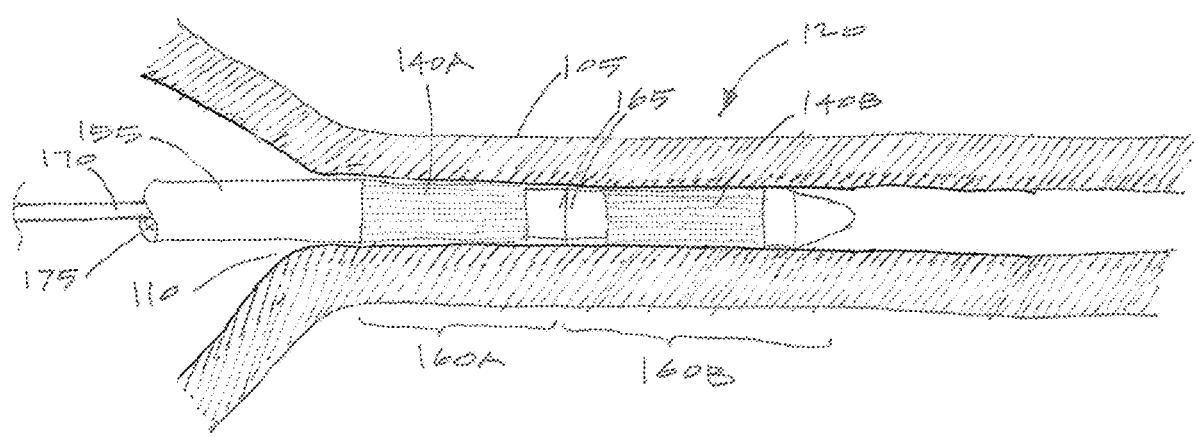
FIG. 2A is a schematic sectional representation of a step of a method of positioning an RF applicator portion of the probe working end in the fallopian tube.
Figure 2B:
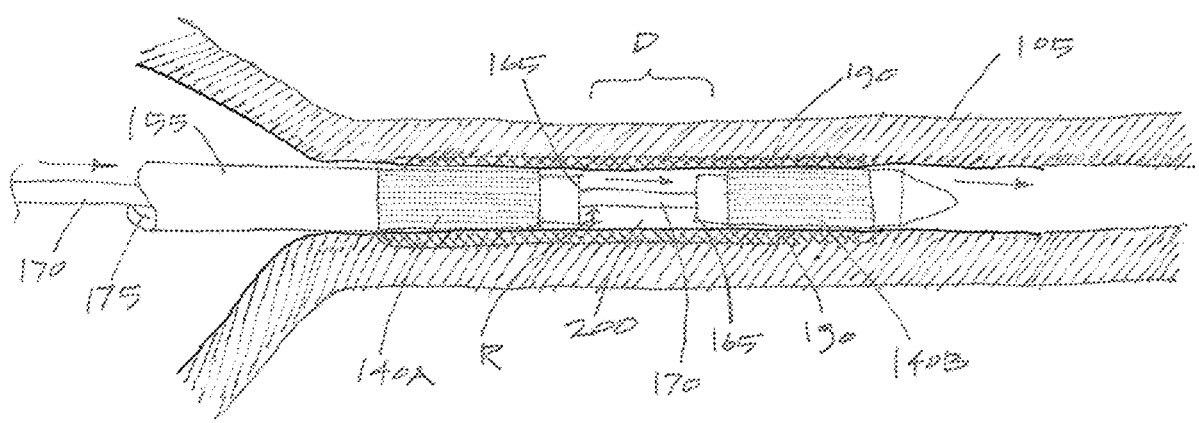
FIG. 2B is another schematic representation of a subsequent step of moving apart proximal and distal body portions of the RF applicator portion of the probe working end, followed by the step of activating RF energy delivery to ablate surface tissue.

Referring now to FIGS. 2A-2B, it can be seen that the working end 120 of probe 125 includes an RF (radiofrequency) applicator which in one variation is spaced apart bi-polar RF electrodes 140A and 140B. The RF applicator is configured to ablate a thin tissue layer within a segment of the lumen of the fallopian tube 105 and optionally a segment in the tubal ostium. The tissue targeted for ablation is the endometrial or endothelial layer. The RF electrode arrangement can consist of a singular opposing polarity electrodes (as shown for convenience) or there can be a plurality of electrodes of each polarity which in any event are configured to provide a selected ablation depth. The axial spacing between bi-polar electrodes 140A-140B and the width of the exposed surface of the electrodes can be adapted to control the ablation depth, which is further dependent on the power level selected and other RF operating parameters. Tissue impedance can be used to terminate power which can be also be used to assist in achieving the selected depth of tissue ablation. An RF generator/controller 150 is electrically connected to the electrodes 140A-140B to provide bi-polar RF energy to the electrode arrangement. As will be described below, both the length of the targeted ablation and the depth of the ablation are controlled in the method corresponding to the invention.

Figure 2C:
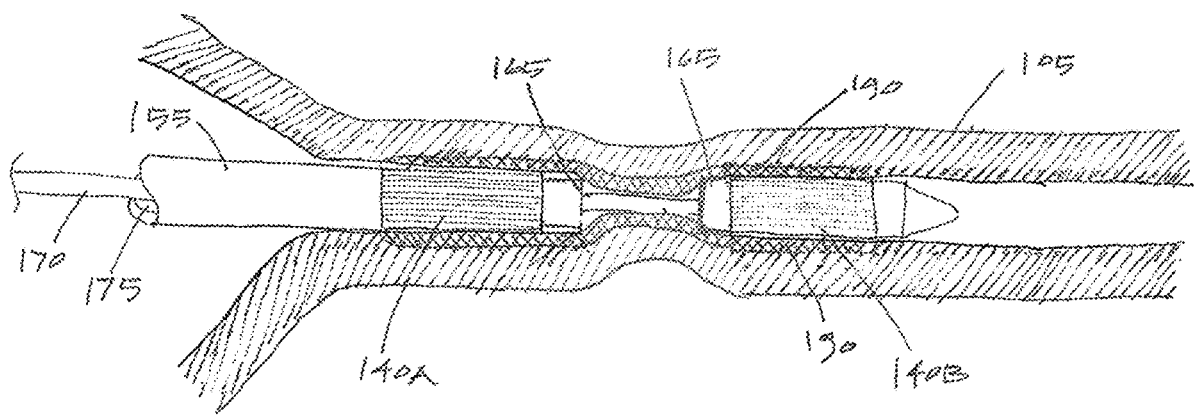
FIG. 2C is a representation of another step of applying suction to draw a tissue segment into a gap between the proximal and distal body portions of the working end to thereby cut surface tissue.

In one variation of a method referring to FIGS. 1-2C, the system (including controller 150 and working end 120) is actuated to deliver RF energy through the RF electrodes 140A and 140B to ablate a selected tissue depth that may range from approximately 0.5 mm to 2.5 mm.

As can be seen in FIGS. 1 and 2A-2B, probe 125 comprises a catheter or elongate flexible shaft 155 that extends to the distal working end 120. The diameter of the catheter 155 and working end can be any suitable diameter and may range from 1 mm to 5 mm.

One variation of working end 120 has proximal body portion 160A carrying electrode 140A and distal body portion 160B carrying electrode 140B. FIGS. 2A-2B illustrate that the proximal and distal body portions 160A, 160B may be axially moveable relative to one another to expose blade edge or edges 165. The central wire member 170 is coupled to the distal body portion 160B and extends to the probe handle 172 (FIG. 1) to allow the physician to manipulate the distal end component. An annular space in the catheter 155 around the central wire member 170 comprises a suction lumen 175 and is coupled to negative pressure source 180. In variations of the device, as shown in FIGS. 2A and 2B, the cutting surface or blade edges 165 are positioned proximally of the distal end of the device to prevent inadvertent damage to tissue when advanced to the target site. Furthermore, the diameter of the cutting surfaces can be less than a diameter of the electrode 140A or 140B (or less than a diameter of the catheter shaft 155) to limit damage to tissue that is drawn into the cutting section (as illustrated in FIG. 2C).

The entire probe may have an interior guidewire lumen (not shown) to allow the probe to be introduced over a guidewire 112.

Referring again to FIGS. 2A-2B, each electrode 140A and 140B (or plurality of electrodes) can have an axial length ranging from about 1 mm to 20 mm. The distance D of the gap 200 between the proximal body portion 160A and distal body portion 160B when moved apart indicated in FIG. 2B also is controlled and can have a dimension ranging from about 5 mm to 20 mm.

FIGS. 2B further shows a subsequent step of the method wherein the system is activated for a predetermined time interval and RF energy creates an ablation zone 190 around the walls of the lumen thus providing a pre-selected length and depth of ablation. The controller can automatically terminate energy delivery based on time, impedance, capacitance, temperature sensing or any combination thereof.

Figure 2D:
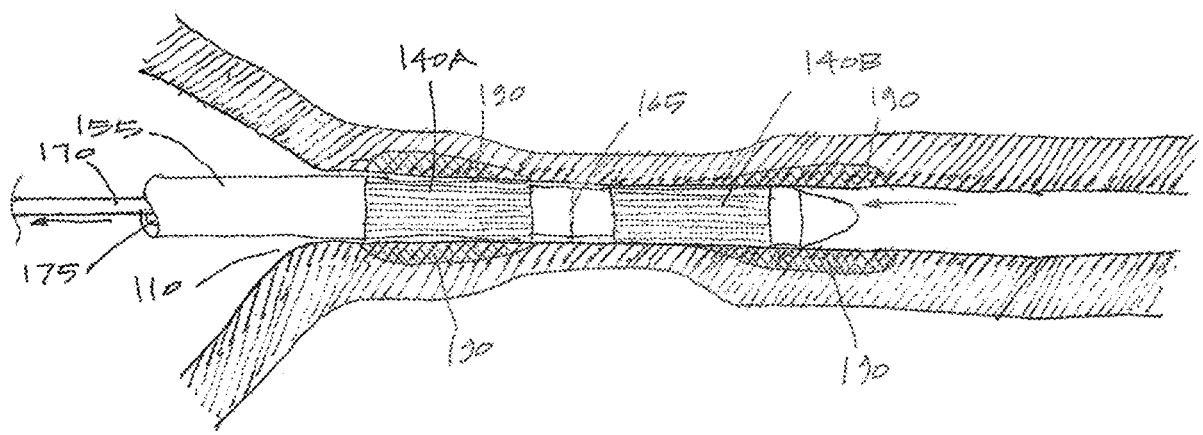
FIG. 2D is a representation of another step of moving together the proximal and distal body portions of the working end to cut tissue captured in the gap shown in FIG. 2C.

FIGS. 2C shows the next step of the method wherein the controller activates the negative pressure source 180 to thus draw tissue into the gap 200 between the blade ends 165 of the proximal and distal body portions 160A, 160B. Next, FIG. 2D illustrates the physician actuating the central wire member 170 to thus move the proximal and distal body portions 160A, 160B together wherein the blade edges 165 approximate to cut tissue suctioned into the gap. The step of cutting tissue may be performed one or more times. The depth of tissue that is cut is controlled by the radial dimension R between the annular blade edge 165 and the diameter of the wire member 170.

Figure 2E:
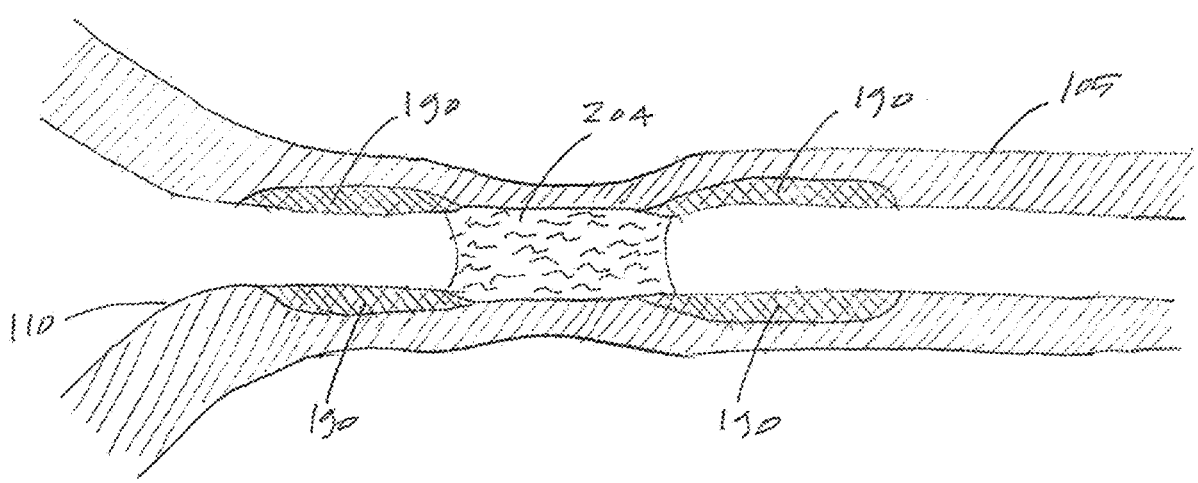
FIG. 2E is another representation showing withdrawal of the working end and the accumulation of blood following the cutting step which initiates a wound healing response to scar across and occlude the lumen.

FIG. 2E illustrates the treated fallopian tube 105 after withdrawal of the working end 120 from the treatment site. It can be seen that the cut or excised tissue causes blood 204 to ooze from the walls from a depth greater than the ablation zone 190. It is this bleeding step that is important to initiate the wound healing response which will result in scarring and an adhesion across the lumen.

Figure 2F:
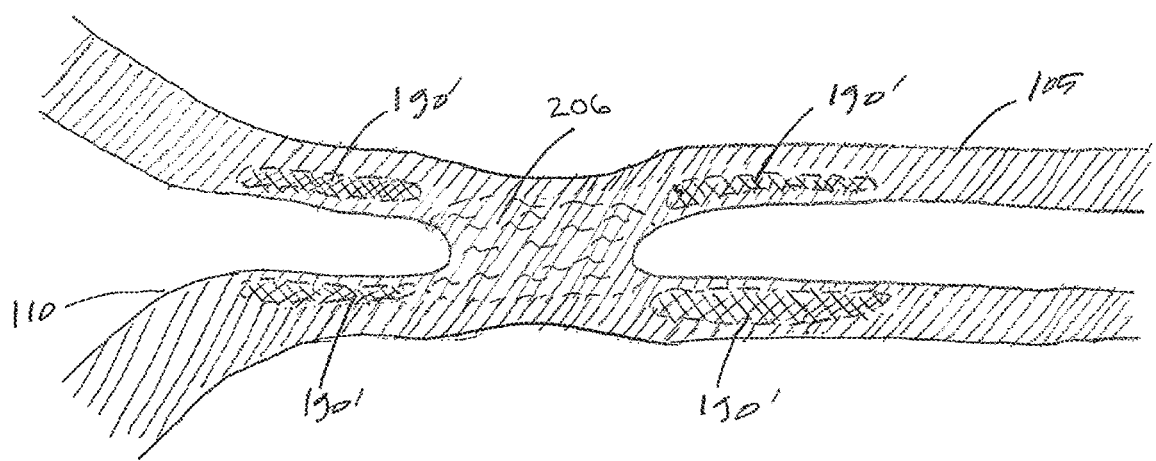
FIG. 2F is another representation after a week or more time has passed showing the adhesion or scar tissue occluding the lumen and the re-growth of endometrial tissue in the lumen up to the adhesion.

FIG. 2F illustrates the adhesion or occlusion after a period of time, for example at least one week. FIG. 2F shows the scar/adhesion tissue 206 across the lumen as fully developed, and the re-growth of endometrial tissue has migrated up the scar or adhesion 206, but such endometrial proliferation was slower than the formation of the adhesion 206 across the lumen. The ablated tissue 190' is shown in the process of being resorbed, which may take from 2 weeks to one month or more.

In one aspect of the method, the adhesion or scar tissue is intentionally created to occlude the fallopian tubes which may be alternatively described as Asherman's syndrome. Such adhesions are internal scars, which are made up of strand-like fibrous tissues forming abnormal bridges/bonds between two parts of the body after trauma through complex processes involving the injured tissues. Asherman's syndrome describes the condition in which scar formation causes the walls of your womb to adhere to one another, which can be triggered by uterine inflammation due to trauma to the endometrium. Scar formation begins immediately after such uterine trauma and it has been reported that scar formation may be complete in about 7 days.

Hormones likely have a role to play in the development of Asherman's syndrome. Estrogen is the hormone that causes the endometrium (uterine lining) to grow and low levels may predispose to the development of scar tissue in the uterus. This is true around the time of pregnancy and breast-feeding when the predominant hormone is progesterone. The high levels of progesterone and the low levels of estrogen create an environment where it is more likely to develop. In the treatment of Asherman's syndrome, estrogen is often used to help the endometrium grow, and it is prescribed in order to thicken the uterine lining quickly. In the method of the invention, hormone modulation also may be used to control the speed at which endometrial cells re-grow over the ablation zone 190 to ensure that scarring and adhesion is complete before the endometrial cells interfere with the occlusion site.

In general, a method for female sterilization corresponding to the invention comprise transcervically inserting a working end of a treatment probe into a fallopian tube, actuating the probe to cause a wound healing response in a targeted adhesion segment of a fallopian tube resulting in adhesion of walls of the tube. At the same time, the probe is actuated to ablate surface tissues in first and second ablation segments on either side of the adhesion segment. The method provides an adhesion segment having a length of at least 1 mm or at least 5 mm. The method further provides that each ablation segment (on both sides of the adhesion segment) has a length of at least 1 mm or at least 5 mm.

In another aspect of the invention, each ablation segment has a length along the lumen that provides for a time interval for endometrial cells to migrate over such an ablation segment, and such interval is at least 2 days and preferably one week.

In another aspect of the method, adhesion segment is treated to provide a wound healing response therein that includes at least one of bleeding, inflammation, macrophage formation, fibroblast proliferation, vascularization, fibrin matrix formation, and scar tissue organization. The treatment of this segment can be provided by at least one of cutting, puncturing, incising or resecting tissue.

In another aspect of the method, the step of ablating surface tissue is provided by at least one of a thermal treatment or cryogenic treatment. Such a thermal treatment can be provided by RF energy, laser or light energy, microwave energy, inductive heating, ultrasound heating, resistive heating. A cryogenic treatment can be provided by a cryogenic fluid flow to the probe working end 120. Clearly any modality of creating the desired tissue effect can be employed in the methods and devices described herein.

As described in one variation above, the adhesion segment can be treated by at least one of a thermal treatment or cryogenic treatment prior to the step of cutting tissue. The cutting step can be performed by a blade edge of any type or performed by a needle-like element to puncture tissue through the depth of the ablated layer. The cut tissue can be captured and removed or not captured.

In another aspect of the method, endometrial cell migration can be modulated by a hormone treatment, for example by oral medication of by introducing drugs or drug-carrying implantable media into the treatment site.

In general, a method for female sterilization comprises ablating the endothelial and/or endometrial cells in an elongated segment of the lumen of a fallopian tube and treating an intermediate portion of said lumen segment to cause Asherman's syndrome in said intermediate portion to thereby occlude the fallopian tube lumen. The step of treating the intermediate portion again includes causing bleeding therein to precipitate the wound healing response as described above.

Figure 3:
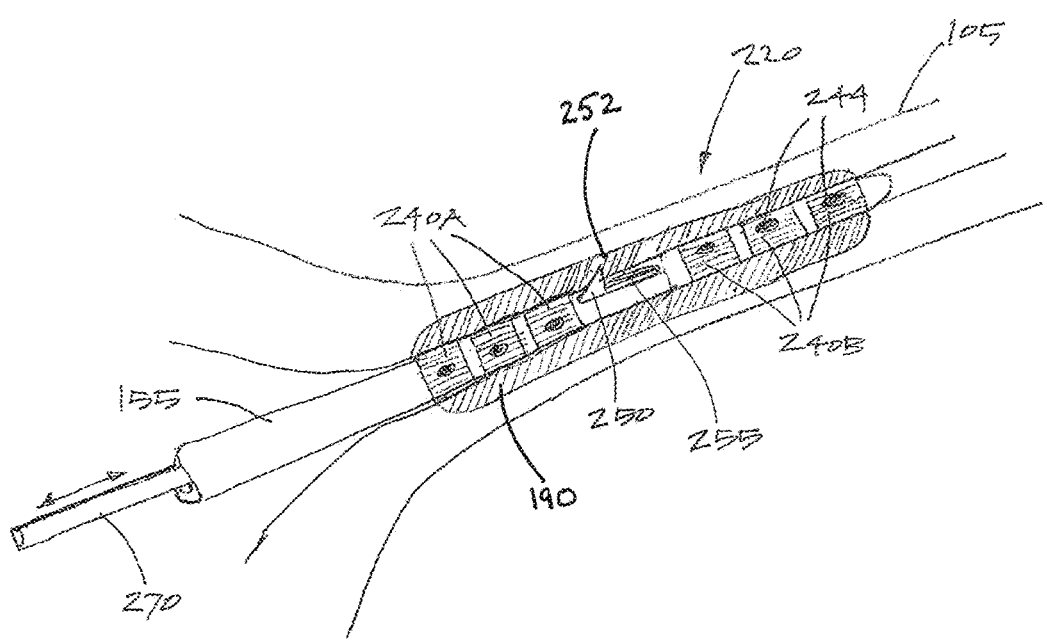
FIG. 3 is schematic representation of another variation of working end for treating tissue in a manner similar to the embodiment and method in FIGS. 2A-2F.

FIG. 3 illustrates another variation of working end 220 that does not have components that move axially apart and together. The working end 220 of FIG. 3 still is adapted to occlude a fallopian tube as described above using the previous embodiment. In FIG. 3, the working end has a plurality of proximal electrodes 240A and has a plurality of distal electrodes 240B. Intermediate the electrodes is a blade element 250 that can be pushed outwardly from slot 255 to cut tissue in this intermediate region 252 of the length of ablated tissue. The blade can be actuated outwardly by push-pull member 270 in the catheter shaft 155. After the RF energy is used to ablate tissue 190, the blade can then be extended outwardly to cut tissue to cause the bleeding step. The working can be move axially or rotationally to assist in the cutting step. In this variation, working end can have suction ports 244 for suctioning tissue against the electrodes. The multiplicity of electrodes can allow multiplexing while changing the polarity of electrodes or groups of electrodes to achieve the desired ablation depth. In this variation and the previous variation, the working end or a portion carrying an electrode can be translated or rotated during RF energy delivery. Following the cutting step of FIG. 3 described above the bleeding will induce the wound healing response and scarring as depicted previously in FIGS. 2E and 2F.

It should be appreciated that any kind of blade edge or needle can be used in the embodiment of FIG. 3 to cause the bleeding step to precipitate the scarring process.

Obviously, the steps described above are performed in both fallopian tubes to provide sterilization.

In another method, as shown in FIGS. 4A-7, an elongated segment of a fallopian tube can be damaged to cause a wound healing response which again causes an adhesion across the lumen of the fallopian tube without requiring ablating the of the cells lining the fallopian tube as described above. In this method, the damage is provided over an elongated longitudinal segment of the fallopian tube lumen, and the adhesion can form and permanently occlude the lumen before new endothelial cells can migrate inwardly from the ends of the damaged segment, which cells are adapted to maintain the patency of the lumen.

Figure 4A:
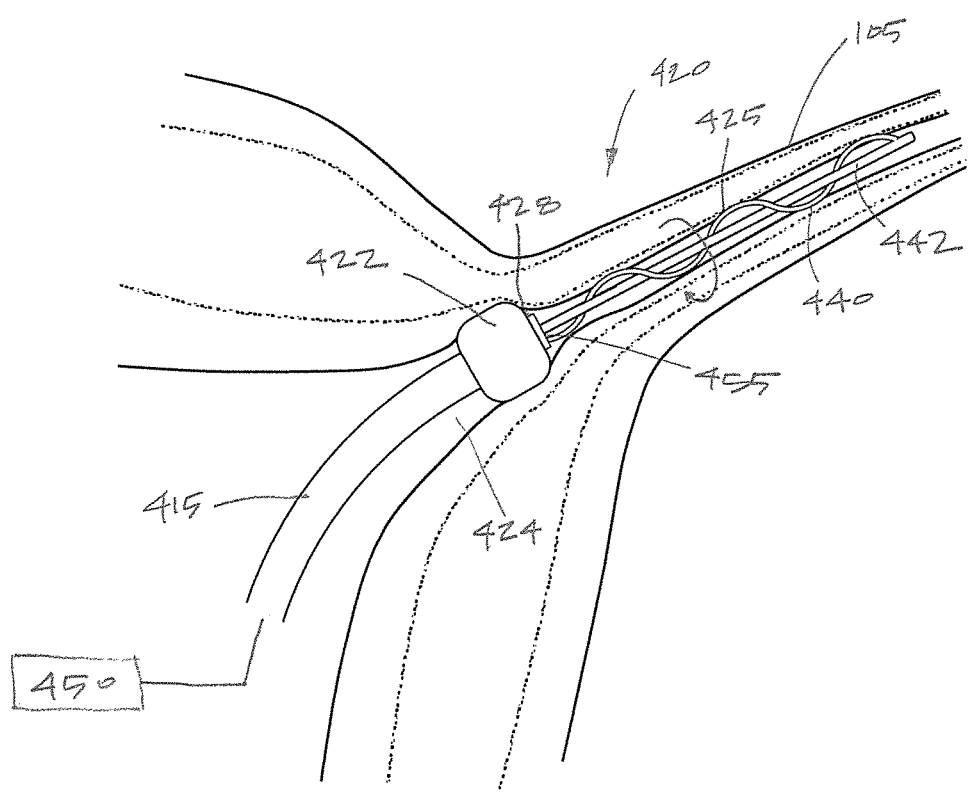
FIG. 4A is an illustration of another variation of a catheter and working end comprising abrading wires.

FIG. 4A illustrates a catheter of probe shaft 415 and working end 420 that is adapted to damage a longitudinal segment of a fallopian tube 105 to cause an adhesion therein which results naturally from the wound healing response as described previously. In FIG. 4A, it can be seen that the catheter shaft 415 carries a balloon 422 that can be expanded by a fluid from a syringe (not shown). The balloon 422 can have any suitable length as required. For example, such lengths can include a range between about 5 mm to 20 mm or more. The balloons may be shaped to fit in a fallopian tube 105 or partly in the ostium 424. In this embodiment, the balloon 422 is used to stabilize the working end 420 in relation to the fallopian tube. Thereafter, an abrading element 425 is exposed at the distal end 428 of the probe, and it can be rotated and/or moved axially to damage the walls of the fallopian tube 105. In the variation of FIG. 4A, the abrading element 425 can be extended from a bore in the shaft 415, or a sleeve can be withdrawn proximally to expose the element 425. The variation of FIG. 4A includes an abrading wire 440 that can be expanded radially outward from a central wire 442 by axial translation of one wire relative to the other. The outward abrading wire 440 then will better conform to and engage the walls of the fallopian tube 105. In one variation, the abrading wire 440 is provided with an abrasive surface which can be deposited on the wire. The wires can be stainless steel, NiTi or any other suitable material. The assembly of wires 440 and 442 then can be fully or partially rotated or moved from the probe handle (not shown) either manually or by a motor at any suitable rpm to abrade the lining of the fallopian tube. In one variation, also shown in FIG. 4A, the catheter can include a negative pressure source 450 communicating with a passageway in the catheter having an open termination 455 distal to the balloon 422, which can be used to suction the lumen walls against the abrading assembly. The abrading wires can have an exposed longitudinal length ranging from about 10 mm to 25 mm or more.

Figure 4B:
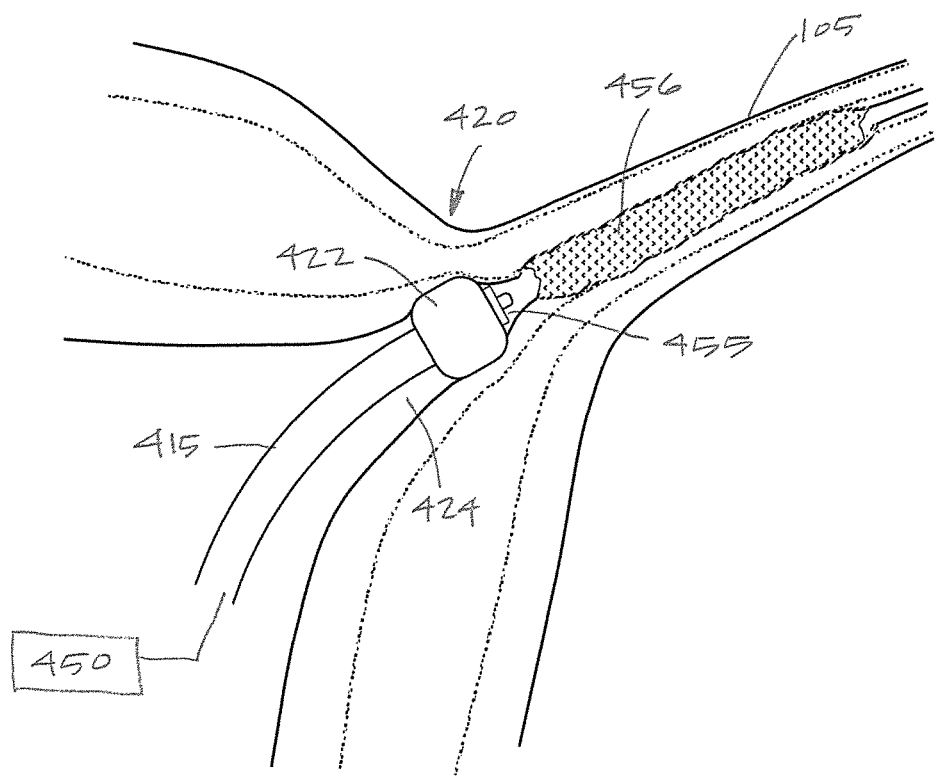
FIG. 4B shows a subsequent step in the method wherein the abrading wire assembly is retracted and blood from the damaged tissue is disposed within the lumen of the fallopian tube.
Figure 4C:
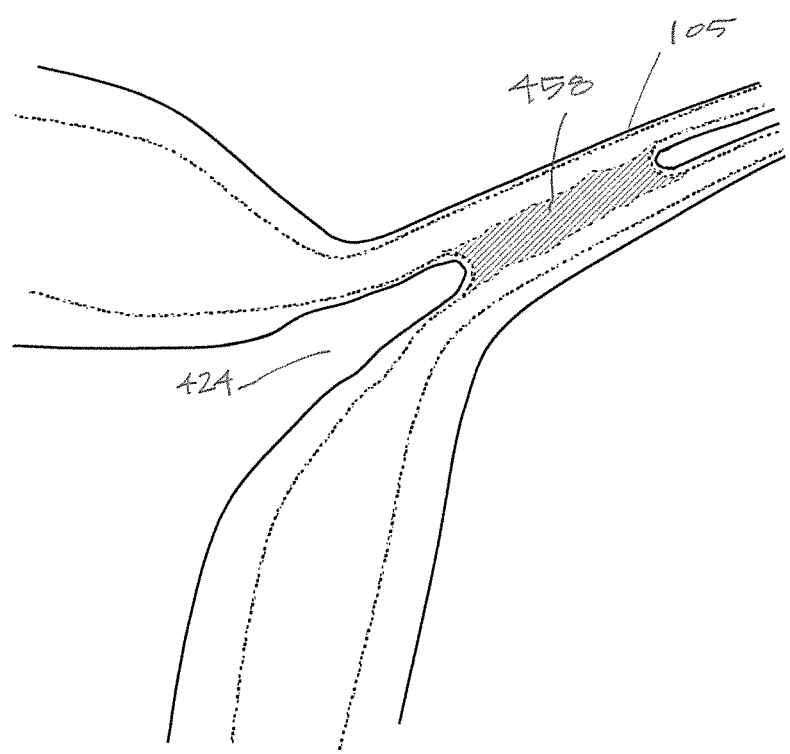
FIG. 4C shows the fallopian tube after the passage of time wherein an adhesion is formed to occlude the lumen of the fallopian tube and endothelial cells have migrated into the lumen from both ends of the treated segment.

FIG. 4B shows a subsequent step in the method wherein the abrading element 425 is withdrawn and blood 456 from the damaged tissue accumulates within the lumen of the fallopian tube 105. FIG. 4C shows the fallopian tube after the passage of time with an adhesion 458 formed to occlude the lumen of the fallopian tube and endothelial cells have migrated into the lumen from both ends of the treated sement.

In general, a method for female sterilization corresponding to the invention comprises transcervically introducing a working end of a treatment probe into a fallopian tube, and actuating the working end to damage a longitudinal segment of the fallopian tube sufficient to cause a wound healing response that thereafter caused adhesion of at least a portion of the segment to permanently close the fallopian tube.

Figure 5:
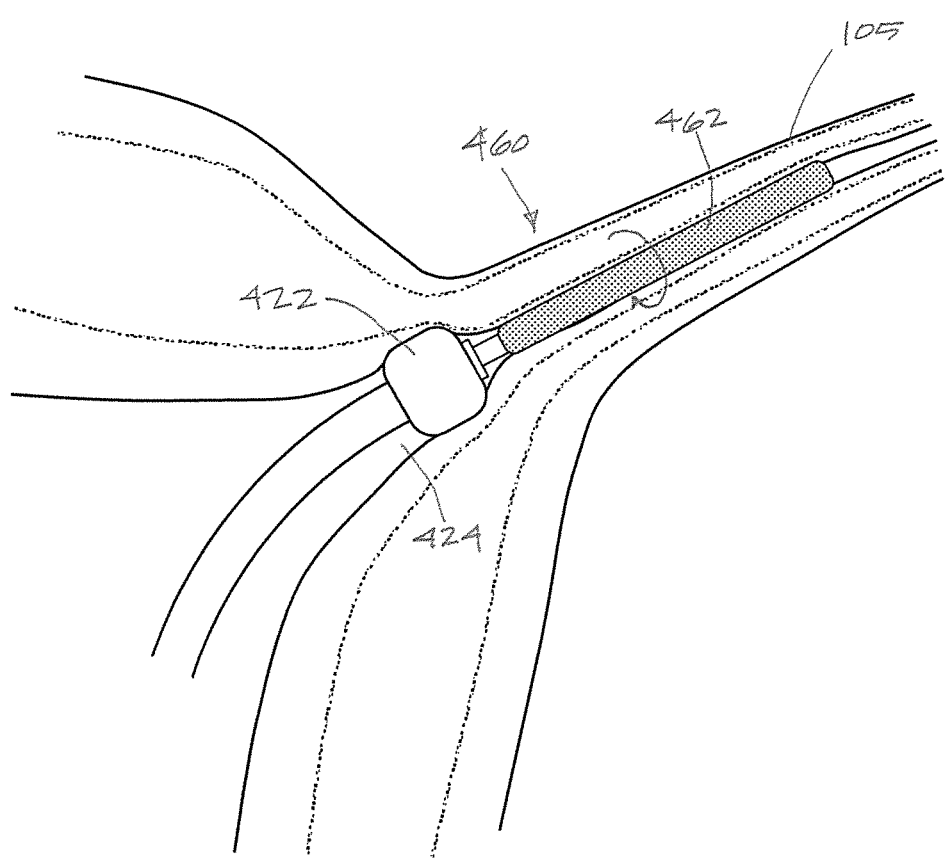
FIG. 5 is a representation of another variation of a catheter and working end including an abrading balloon that is adapted for abrading the surface layers of the lumen of a fallopian tube.

In another variation shown in FIG. 5, the catheter has a working end 460 that again is adapted to abrade tissue and comprises a rotatable expandable balloon 462. The balloon 462 can have an abrasive surface or one or more lines of an abrasive material that can be expanded radially outward. The working end 460 again carries an expandable positioning balloon 422 as in the previous embodiment that is proximal to the rotatable abrading balloon. In another variation (not shown) a second distal balloon can be carried by the working end 460 that is distal to the abrading balloon 462 to thus stabilize both the proximal and distal regions of the fallopian tube 105 on either side of the segment targeted for treatment and damage. In another variation (not shown), the catheter can have proximal and distal stabilizing balloons, and a rotatable non-balloon abrading element intermediate the two stabilizing balloons. The rotatable abrading element can be a wire assembly, as shown in FIG. 4, a balloon that pushes wires or blades outwardly, an articulating member or simply a straight wire with a curved repose (non-tensioned) shape that can be rotated to abrade tissue. The negative pressure source 450 described above can be used to suction tissue against the abrading or cutting element between such proximal and distal stabilizing balloons. In the variation of FIG. 5, it can be understood that the damaged tissue will result in a wound healing response and adhesion, as shown in FIGS. 4B-4C.

In another aspect of the invention, the method includes applying negative pressure from source 450 to the treatment site to cause bleeding in the site (cf. FIG. 4B). Such bleeding contributes to the wound healing response that in turn causes the formation of an adhesion in the treatment site.

Figure 6:
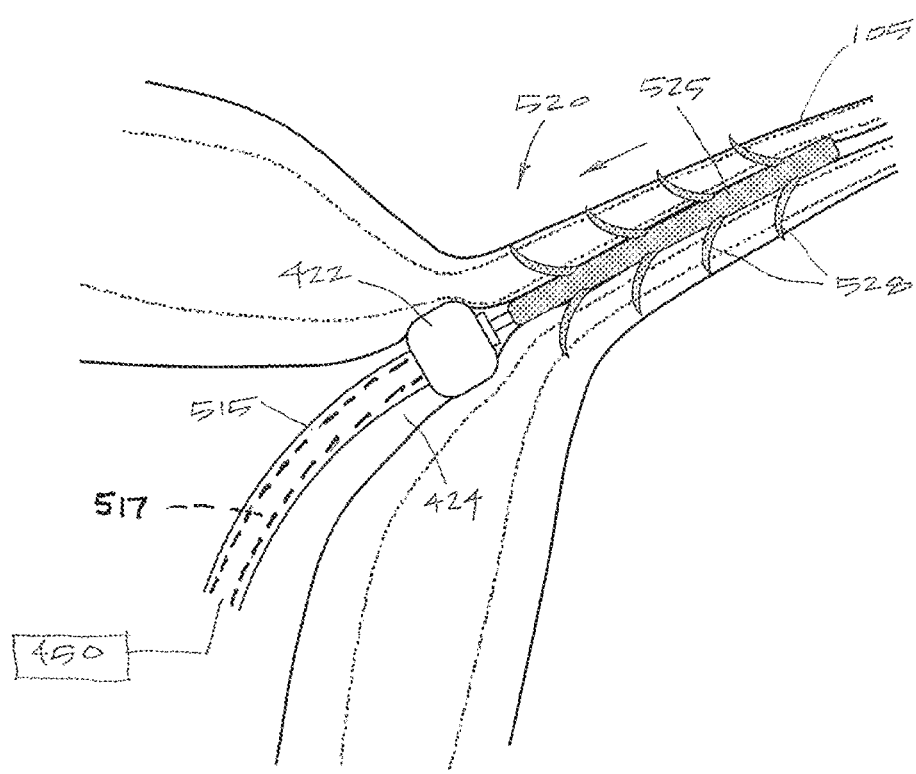
FIG. 6 is a representation of a catheter working end that carries a deployable barbed implant that is adapted for puncturing and damaging the walls of the lumen of a fallopian tube.

In another variation of the invention shown in FIG. 6, the catheter has shaft 515 and working end 520 that carries a deployable barbed implant 525 that is configured to cause barbs 528 to puncture the walls of the fallopian tube 105 to thus induce a wound healing response. The implant 525 can be carried in a bore in the catheter shaft 515 and can be pushed outwardly to thus cause the resilient barbs 528 to project radially outward. The assembly then can be actuated to move the implant 525 proximally to cause the barbs 528 to penetrate the walls of the fallopian tube 105. In this variation, the stabilizing balloon 422 again can be used as in the previous embodiments of FIGS. 4A-5 to engage the walls of the fallopian tube 105 prior to the step of moving the implant 525 to cause the barbs 528 to penetrate tissue. The length of the implant can be from about 5 mm to 20 mm or more. The negative pressure source 450 can be used to cause bleeding as described above from the sites where the barbs 528 penetrate tissue. The number of barbs can range from 2 to 100 or more.

The implant of FIG. 6 can be formed of any biodegradable or bioresorbable polymer known in that art or it can be a metal implant made of a suitable material such as NiTi. Alternatively, the implant 525 can be a combination of a polymer and a metal. The material can be porous or microporous to allow rapid ingrowth of fibrotic material.

Figure 7:
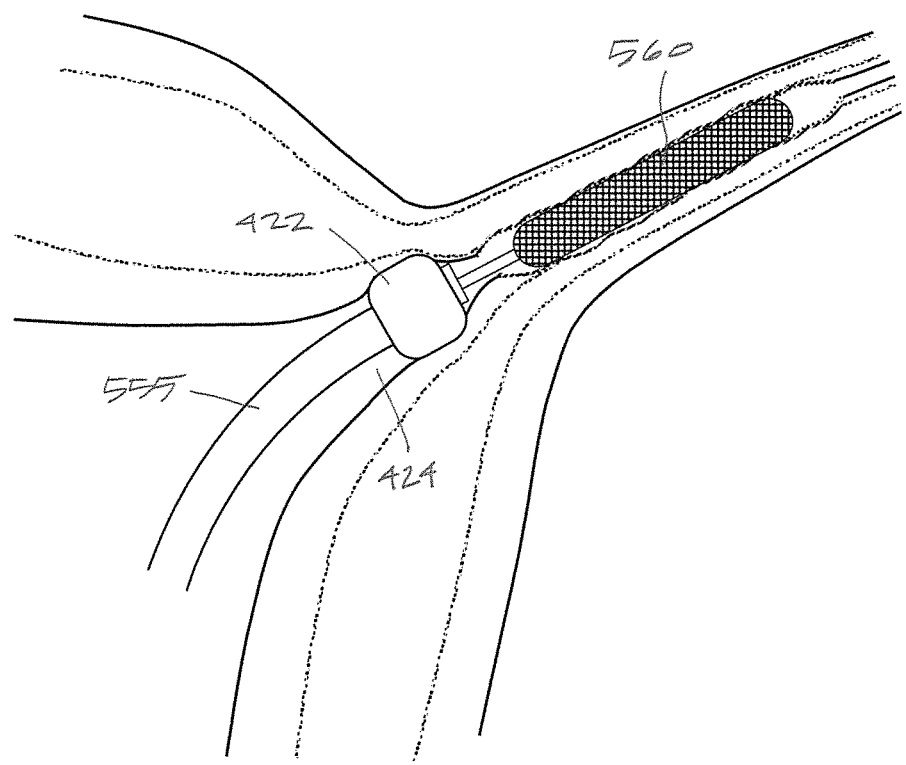
FIG. 7 is a representation of a catheter working end that has deployed an implant that is adapted to promote an adhesion across the lumen of a fallopian tube.

In another aspect of the invention shown in FIG. 7, a catheter with shaft 555 can deploy a porous, microporous or nanoporous implant 560 following an abrading step (typically using a different catheter) as described previously. Such an implant 560 can carry a pharmacological agent adapted to accelerate fibrosis in the treated segment. In another aspect, end portions of such an implant 560 can carry pharmacological agents to inhibit or degrade the migration of endothelial or endometrial cells, and the central portion of the implant 560 can optionally carry drugs to promote fibrosis. Any suitable polymers can be used that are infused with pharmacological agents. Alternatively, strands of material such as in electrospun filaments can be used to form the implant 560.

While the above FIGS. 4A-6 have shown various catheter working end adapted to damage tissue, it should be appreciated that any mechanical structure having abrasive features, cutting features, penetrating features and/or puncturing features that can cut, incise, resect, abrade, damage, puncture or de-nude the surface or in the fallopian tube wall fall within the scope of the invention.

A number of embodiments of the invention have been described. Nevertheless, it will be understood that various modifications may be made without departing from the spirit and scope of the invention.

What is claimed is:

1. A method for occluding a fallopian tube, comprising:
    advancing a probe trans-cervically to a site in the fallopian tube such that a first electrode is spaced by a gap from a second electrode in the fallopian tube;
    applying energy from the first electrode and the second electrode to form an area of ablated fallopian tube tissue at the site;
    actuating a cutting surface coupled to the probe and being positioned between the first electrode and the second electrode to cause a bleeding at the area of ablated fallopian tube tissue wherein the bleeding facilitates adhesion of walls of the fallopian tube to provide permanent occlusion; and
    withdrawing the probe from the site in the fallopian tube.

2. The method of claim 1 wherein advancing the probe includes advancing the probe over a guidewire.

3. The method of claim 1 wherein applying energy includes at least one of applying RF energy, light energy, microwave energy, resistive heating, inductive heating or ultrasound.

4. The method of claim 1 wherein actuating the cutting surface includes actuating at least one of a sharp blade edge, an abrasive element and a sharp puncturing element.

5. The method of claim 1 further including deploying a bioabsorbable implant in the site.

6. The method of claim 1 wherein actuating the cutting surface causes the bleeding in an intermediate region of the area of ablated fallopian tube tissue.

7. The method of claim 1, wherein the cutting surface comprises at least a first sharp cutting edge carried by a moveable outer sleeve.

8. The method of claim 7, wherein the cutting surface is intermediate to the first electrode and the second electrode spaced apart at a working end of the probe.

9. The method of claim 7, wherein the cutting surface includes an inner member disposed in a passageway of the moveable outer sleeve.

10. The method of claim 1, further comprising applying suction through the probe at the site.

11. The method of claim 1, wherein applying energy further includes terminating energy delivery in response to at least one of time, impedance, capacitance, and temperature.

12. The method of claim 1, wherein applying energy comprises providing energy by at least one of a thermal treatment or a cryogenic treatment.

13. The method of claim 12, wherein the thermal treatment comprises an energy source selected from a group consisting of RF energy, light energy, microwave energy, resistive heating, inductive heating and ultrasound.

14. The method of claim 1, wherein the cutting surface includes at least one of a sharp blade edge, an abrasive element and a sharp puncturing element.

15. The method of claim 1, wherein the probe carries an expandable balloon, the method further comprises expanding the expandable balloon at the site.

16. The method of claim 1, further comprising deploying an implant at the site.

17. The method of claim 16, wherein the implant comprises a biodegradable or a bioresorbable polymer.

18. The method of claim 16, wherein the implant has at least one barb.

19. The method of claim 16, wherein the implant is porous.

* * * * *